United States Patent
Kaplan

Patent Number: 5,920,393
Date of Patent: Jul. 6, 1999

[54] METHODS AND APPARATUS FOR IDENTIFYING AND QUANTIFYING CONSTITUENT COMPOUNDS IN A SPECIMEN USING MODULATED POLYCHROMATIC PARTIALLY POLARIZED LIGHT

[76] Inventor: Milton R. Kaplan, 1523 Hawks Meadow, San Antonio, Tex. 78248

[21] Appl. No.: 09/169,082

[22] Filed: Oct. 8, 1998

Related U.S. Application Data

[63] Continuation-in-part of application No. 08/392,728, Nov. 22, 1995.

[51] Int. Cl.$^6$ .............................. G01J 4/00; A61B 5/00
[52] U.S. Cl. ..................... 356/364; 600/316; 600/322; 356/367
[58] Field of Search .................................. 356/364, 365, 356/367, 366, 368, 39, 40; 60/316, 322; 250/225

[56] References Cited

U.S. PATENT DOCUMENTS

| | | | |
|---|---|---|---|
| 3,724,952 | 4/1973 | Vossberg | 356/366 |
| 4,011,014 | 3/1977 | Tanton | 356/367 |
| 4,901,728 | 2/1990 | Hutchison | 356/368 |
| 5,009,230 | 4/1991 | Hutchinson | 356/368 |
| 5,209,231 | 5/1993 | Cote et al. | 356/367 |
| 5,687,721 | 11/1997 | Kuhls | 356/364 |

Primary Examiner—Hoa Q. Pham
Attorney, Agent, or Firm—Kammer & Huff, PLLC

[57] ABSTRACT

Methods and devices for determining the identity and concentration of constituent compounds within a test specimen. The methods are based on the principle that a specific compound in a specific concentration will modify a pattern of incident polychromatic light in a manner that is recognizable. The system includes a polychromatic light source directed first through an incident light pattern generator and then through the test specimen. Reflected and transmitted light components then pass through a pattern recognition gating device that selects portions of the light for analysis by an array of detectors. The methods include producing a modulated pattern of incident light specific for a particular compound of interest and selectively analyzing the reflected or transmitted light according to known patterns for that compound in specific concentrations. Modulated incident light patterns include variations in wavelength (typically non-absorbing for the compound), variations in partial polarization, as well as modulation of phase, amplitude, sampling frequency, and polarization frequency. The selective pattern analysis includes spectral scanning for identification of specific wavelength amplitudes as well as a second polarizer for accurately identifying polarization shifts. The detector array identifies specific scattering angles associated with each of the various analyzed light conditions. The patterns are sufficiently unique to be recognizable for a given compound regardless of the presence of additional compounds within the test specimen.

2 Claims, 5 Drawing Sheets

METHODS AND APPARATUS FOR IDENTIFYING AND QUANTIFYING CONSTITUENT COMPOUNDS IN A SPECIMEN USING MODULATED POLYCHROMATIC PARTIALLY POLARIZED LIGHT

This application is a CIP of application Ser. No. 08/392,728, filed Nov. 22, 1995.

BACKGROUND OF THE INVENTION

1. Field of the Invention

The present invention relates generally to the field of polychromatic spectroscopic analysis of test specimens to determine the identity and concentration of constituent elements or compounds within the specimen. The present invention relates more specifically to methods and apparatus for utilizing optical transmission and reflection patterns for known compounds, patterns comprising variations in wavelength, phase, amplitude and polarization, to identify and quantify those compounds in unknown test specimens.

2. Background Information

Presently, there are a number of distinct methods employed for identifying constituent compounds in a test specimen and determining the concentration of each compound. Chemical analysis of a specimen, for example, is frequently undertaken and usually yields excellent results. However, certain specimens, including internal bodily fluids, are not particularly suited for chemical analysis, because such specimens can only be chemically analyzed by undertaking an invasive procedure—such as drawing blood—that may be painful and entail a risk of infection. For this reason, an accurate, non-invasive analytical method is needed for determining the identity and concentration of various compounds, such as glucose, alcohol or narcotic substances, in internal bodily fluids, such as blood.

SPECTROPHOTOMETRIC ANALYSIS

Among the more useful tools for performing non-invasive analytical procedures is the use of spectrophotometric analysis. Spectrophotometric analysis relies on the principle that every compound has a unique "pattern" determined by the amount of light absorbed, transmitted, or reflected by the compound at various wavelengths. Typically, analytical spectrophotometric methods target the specimen with light of known intensity, wavelength, and phase, and then measure the absorption of light by the specimen, at various wavelengths, or conversely, measure the intensity of light passing through the specimen, at various wavelengths, and then compare this "pattern" of absorption (or transmission) at different wavelengths with the known pattern of absorption of various compounds.

Unfortunately, most types of spectrophotometric analysis are only of limited usefulness when the specimen is complex, (i.e. contains several compounds or elements), or when the density of the specimen is unknown. These limitations are present because the absorption of light (or the intensity of transmitted light) may be directly affected by these variable factors. Thus, relying solely on the absorption of light at various wavelengths does not yield a sufficiently accurate non-invasive method for analysis of bodily fluids. Certainly, the detection and measurement of other optical factors, which are unique for each compound, in addition to measurement of the absorption of light by the specimen for various wavelengths, would greatly improve the efficiency and accuracy of any spectroscopic technique used for determining the identity and concentration of constituent elements in a specimen.

POLARIMETRIC ANALYSIS

In an attempt to provide more accurate testing and to overcome other limitations of conventional spectrophotometric analysis of a specimen, several procedures have been developed using polarimetric analysis. Polarimetric analysis uses polarized light rather than randomly polarized (or "unpolarized") light to irradiate the test specimen and relies on the principle that specimens containing an optically active compound, such as glucose, will rotate the plane of polarized light, thereby causing a measurable "shift" in the plane of polarization. The degree and direction of the polarization shift that may be caused by a compound is unique for each compound. In addition, certain compounds "depolarize" polarized light in a unique manner.

Thus, by irradiating a test specimen with light that is polarized in a predetermined plane and then measuring the polarization shift and/or the degree of depolarization of the light caused by the constituent components of the specimen at various wavelengths, the identity of the components in a specimen as well as the respective concentrations of the components, theoretically can be more readily determined than by measuring only the absorption of light per wavelength.

Examples of prior-issued patents that are known to Applicant, which address the use of polarized light in performing a spectroscopic analysis of a specimen, include the following:

U.S. Pat. No. 3,724,952 issued to Vossberg on Apr. 3, 1973, describes an apparatus and method for polarimetric analysis of a specimen, comprising the use of light that is polarized in one plane prior to passage of the light through the specimen. After the polarized light passes through the specimen, it passes through an analyzer and detector, which determine the "polarization shift" caused by the components of the specimen, as well as the degree of depolarization and the absorption of light by the specimen.

U.S. Pat. No. 4,901,728 and U.S. Pat. No. 5,009,230 issued to Hutchinson on Feb. 20, 1990 and Apr. 23, 1991, respectively, describe a device for non-invasive determination of blood glucose of a patient, by passing two orthogonal and equally polarized states of infrared light of the same intensity through a specimen and then passing the light through a polarizer to determine the rotation of the polarized light caused by the glucose in the specimen. The polarization shift is measured by calculating the difference in intensity of the two states of polarized light exiting the polarizer.

U.S. Pat. No. 4,011,014 issued to Tanton on Mar. 8, 1977 describes a device for testing the rotation of polarized light by translucent specimens. The device includes a polarizer to polarize light prior to the light contacting the specimen, and then measures the polarization shift and other optical factors, that are caused by the specimen.

U.S. Pat. No. 5,687,721 issued to Kuhls on Nov. 18, 1997 describes a device and method for non-invasively measuring the concentration of sugar in the blood. The method includes directing a beam of monochromatic light through a polarizer to the test specimen. The method then includes performing both a static extinction measurement using the monochromatic light and a dynamic polarization measurement using the polarized light.

Each of the above-described methods and apparatus for polarimetric analysis rely upon the principle of irradiating the specimen with light that is already polarized in a predetermined plane, and then measuring the polarization shift or other variables caused by the rotation of the polarized light by optically active compounds in the specimen. Although measuring the "polarization" shift and/or other data dependent on the rotation of polarized light by the specimen does provide certain information that can be objectively analyzed, the use of light that already is polarized to irradiate the specimen has severe drawbacks, in addition to the limitations presented by standard spectrophotometric analysis.

First, polarizing the light prior to irradiating the specimen significantly decreases the amount of light actually reaching the specimen. This is because a percentage of the light will be reflected or absorbed by the polarizing means before the light reaches the specimen. Obviously, when the specimen is dense, this loss of light could dramatically impact the amount of light actually passing through the specimen and capable of being measured.

In addition, polarizing the light in a particular plane of polarization before the light reaches the specimen, effectively eliminates all other planes of polarization in which the light travels, thereby drastically reducing the potential data that could be gathered if the light targeted on the specimen was partially polarized light. In essence, trying to identify a compound in a complex specimen, by considering only the optical factors of light traveling through the specimen in a single plane of polarization unnecessarily eliminates a large portion of the interrogating light and the wealth of information that portion of the light might provide.

The inadequacy of the limited information obtained by using polarized light to irradiate a specimen is especially evident when the specimen contains two or more compounds. Because the compounds may cause similar polarization shifts in the specific polarization plane in which the light is polarized, it becomes very difficult to determine the identity and concentration of the different compounds in the specimen. The presence of more than one compound in the specimen may also "mask" the polarization shift that is caused by the targeted compound because the presence of other compounds in the specimen may cause an enhancement or decrease in the polarization shift at the specific polarization plane in which the light is polarized. This masking effect on the polarization shift may cause either the identity or the concentration of the targeted compound to be incorrectly determined.

As briefly shown by the foregoing, both conventional spectrophotometric analysis and polarimetric analysis of a test specimen are severely hampered by the limited amount of data that can be obtained by merely measuring the absorption of light for various wavelengths or by using polarized light to irradiate the specimen. Clearly, a method and apparatus is needed that would identify and accurately measure a wider range of optical factors than is possible by using standard spectrophotometric analysis or polarimetric analysis.

A starting point to the solution of the problem lies in the well developed electro-optical probe technologies currently in use in university, industrial, and government laboratories. The sensitivity of such probes may be increased enormously by taking advantage of the wavelength dependency of polarized light. All wavelength components of polychromatic light may become polarized, but not in the same way, and each must be examined separately. Each wavelength responds differently to a specific optically active medium.

COMPLEX POLARIMETRIC ANALYSIS

After adding to the analysis distinctions regarding wavelength, it is advantageous to add the more complex aspects of the polarization rotational characteristics that result from the irradiation of many substances, especially organic. In general, organic molecules are structured in spiraled form and have a definite helicity or handedness. It is this helicity which gives a molecule its ability to rotate the polarization of the incident light. For example, dextrose (d-glucose) is, by convention, right-handed since, when viewed from the perspective of light emerging from the sample, the polarization axis has rotated in a clockwise direction. On the other hand, levulose (fruit sugar) is left-handed since it rotates the polarization axis in a counter clockwise direction. Molecules or material which exhibit this kind of optical activity are said to possess optical rotary power. In particular, these are termed dextrorotary or levorotatory respectively depending upon the action on the polarization of the incident light. The magnitude of the angle, through which the polarization direction rotates is, in simple theory, proportional to the inverse of the wavelength of the incident light squared. Sometimes called a dispersion function, this relationship is weakly dependent on wavelength but is strongly a function of the type of material or molecular structure being irradiated.

This functional dependence on the physical properties of the medium manifests itself in the different indices of refraction for right- and left-handed polarized light. Two circularly polarized waves of opposite helicity form a set of basic fields for the description of any general state of polarization. As a result, for example, if the polarization of the light irradiating the sample were purely elliptical not only would the ellipse rotate about an axis parallel to the direction of propagation of the light, but the ellipse would also become distorted, i.e. its eccentricity will change. This latter phenomenon is called circular dichroism, and is due to differences in the absorption of right- and left-handed circularly polarized light.

In a fluid, where there is no long-range order, the molecules are randomly oriented. Nevertheless, the effect of rotary power is not averaged out to zero. Since the constituent molecules all have a definite helicity which is the same, they cannot be brought into coincidence with their mirror images—they are enantiomorphous. Thus, the effect of the rotary power of an individual molecule is enhanced in a fluid state. Substances which exhibit both optical rotary power and circular dichroism are referred to as chiral media.

A glucose solution is an isotropic chiral substance. When plane-polarized light impinges normally on glucose the vibration ellipse of the transmitted light is different from the vibration ellipse of the incident light. The difference is characterized by two quantities: (i) Optical Rotation (OR), which is the angle by which the transmission ellipse rotates with respect to the incidence ellipse; and (ii) Circular Dichroism (CD), which is a measure of the difference in the eccentricities of the two ellipses.

Profiles of the OR and the CD of an isotropic chiral substance with respect to frequency are sufficiently unique that they can be used as a component in the signature of a substance to be identified. Because the OR and the CD of specific substances have been shown to be Kramers-Kronig-consistent, complete knowledge of either of the two quantities as a function of the frequency of the light is sufficient to determine the other. Therefore, the more easily measured OR is often used to characterize isotropic chiral substances.

An example of the application of the above principles to a biological sample with a glucose component is instructive. A first issue relates to polarization. Let us suppose that the incident light is a planewave traveling in the +z direction (of a Cartesian coordinate system) at a frequency f. The electric field phasor associated with this planewave may be adequately set up as $$E_{inc}(z,t)=[A_x\,u_x+A_y\,u_y]\,e^{-i2\pi f(t-z/c_o)}, \tag{1}$$

where t is time and $c_o=3\times10^8$ m/s is the speed of light in free space; $i=\sqrt{(-1)}$; $(u_x, u_y, u_z)$ are the unit Cartesian vectors; and $A_x$ and $A_y$ are complex amplitudes with units of V/m.

Let the complex amplitudes be independent of time t. In general, Equation (1) then represents an elliptically polarized planewave whose vibration ellipse does not change with time t. When either $A_x=0$ or $A_y=0$, the planewave is said to be linearly polarized. When $A_x=\pm iA_y$, the planewave is circularly polarized.

Suppose now that $A_x$ and $A_y$ are functions of time t. Then Eq. (1) should be rewritten as $$E_{inc}(z,t)=[A_x(t)u_x+A_y(t)u_y]\,e^{-i2\pi f(t-z/c_o)}. \tag{2}$$

Equation (2) still denotes a planewave, but one whose vibration ellipse changes with time t. Complicated sources have to be utilized in order to deliver specific $A_x(t)$ and $A_y(t)$. Indeed, the prior art devices utilize complicated light sources that yield $A_x(t)$ and $A_y(t)$ as controllable functions of time t.

The present invention, however, utilizes a source (or sources) based on a Quartz-Tungsten-Halogen (QTH) lamp whose output in the focal region is partially polarized. Other suitable light sources include devices which emit light at multiple frequencies, such as LEDs. To understand the term "partially polarized", it is best to begin by thinking about "totally unpolarized" planewaves. The functions $A_x(t)$ and $A_y(t)$ are continuously random functions of time for a totally unpolarized planewave, therefore the rotation of a totally unpolarized planewave by a glucose cell cannot be measured and even the concept is of no meaning.

A partially polarized planewave can be thought of as a combination of a totally unpolarized planewave and an elliptically polarized planewave. The second component of the partially polarized wave suffers a definite rotation on passage through a glucose cell, therefore can be used for OR measurements.

The present invention has a source that delivers a slightly polarized planewave, thus its rotation by the glucose cell is meaningful.

A second issue that must be addressed is that of chromaticity. The devices described in the prior art ideally need monochromatic sources, i.e., sources whose outputs are fixed at precisely one frequency. Practical monochromatic sources cannot be ideal, instead their frequency range is very small.

Suppose $f_c$ is the center-frequency of a source and its 3-db bandwidth is denoted by $\Delta f$; then, we can define a quality factor $$Q=f_c/\Delta f. \tag{3}$$

The QTH lamp used in the preferred embodiment of the present invention is a white-light lamp operating from 400 to 2000 nm with a peak at 900 nm; thus, its useful frequency spectrum ranges from $1.5\times10^{14}$ Hz to $7.5\times10^{14}$ Hz with its peak intensity at $3.3\times10^{14}$ Hz. As the QTH output is roughly independent of the frequency over the operating range, we can estimate its Q=3.3/(7.5-1.5)=0.55. Thus, the QTH lamp is definitely a polychromatic source.

The present invention also utilizes a polarization-preserving analyzer whose response is flat over the $2.3\times10^{14}$ Hz to $4.3\times10^{14}$ Hz range, and it uses a compensated polychromatic detector to measure the intensity of the beam transmitted by the analyzer. In sum, the present invention is polychromatic (low-Q), while the devices described in the prior art are monochromatic (high-Q).

Polychromaticity has a definite advantage over monochromaticity for such things as blood glucose measurements. The OR spectrum of a chiral solute in a non-chiral solvent depends on the concentration of the solute. The amount of glucose in a biological sample (diabetic for example) varies with time and from sample to sample. This means that the OR spectrum of a diabetic sample shifts with time. A polychromatic system therefore has a much better chance of monitoring a continuously varying non-normoglycemic sample than a monochromatic one.

SUMMARY OF THE INVENTION

It is therefore an object of the present invention to provide a novel apparatus and method for accurately determining the identity and concentration of compounds contained in a test specimen.

It is another object of the present invention to provide a non-invasive apparatus and method for accurately determining the identity and concentration of compounds contained in a test specimen.

It is a further object of the present invention to provide an apparatus and method for spectroscopic analysis of a specimen that is able to identify and accurately measure a wider range of optical patterns than is possible by using standard spectrophotometric analysis or polarimetric analysis.

It is another object of the present invention to provide an apparatus and method that permit accurate, non-invasive detection and concentration measurement of substances carried in the bodily fluids of a test subject.

It is another object of the present invention to use polychromatic, partially polarized light, to irradiate a test specimen during spectroscopic analysis, so as to maximize the transmission and/or reflection of light from such specimen.

It is a further object of the present invention to provide a non-invasive apparatus and method which maximizes the transmission and/or reflection of light from a test specimen undergoing spectroscopic analysis, so as to provide increased useful data concerning light emissions from the specimen in multiple planes of polarization and multiple pattern characteristics.

It is another object of the present invention to provide a non-invasive apparatus and method for accurately determining the identity and concentration of compounds contained in a test specimen, by using polychromatic, partially polarized light to irradiate the test specimen and determining the extent to which the randomly polarized light is naturally polarized by the constituent components of the test specimen.

It is another object of the present invention to provide a non-invasive apparatus and method for accurately determining the identity and concentration of compounds contained in a test specimen, by using polychromatic, partially polarized light to irradiate the test specimen and analyzing the manner in which modulated patterns of incident light are modified by the test specimen through the detection and analysis of the transmitted and/or reflected light patterns.

It is a further object of the present invention to provide a non-invasive apparatus and method that uses polychromatic, partially polarized light modulated according to specific optimal patterns to irradiate a test specimen during spectroscopic analysis and thereafter analyzing modifications brought about within the transmitted and/or reflected light from such specimen, thereby identifying the identify and concentration of constituent compounds within the specimen by association of the pattern modifications with previously determined patterns.

In satisfaction of these and related objectives, Applicant's present invention teaches a novel non-invasive method and apparatus for identifying and quantifying compounds in a test specimen, such as blood, by irradiating the test specimen with polychromatic, partially polarized light and then measuring the intensity of light passing through or reflected from the specimen at various degrees of polarization, at various wavelengths and at various times during irradiation.

Unlike the methods and apparatus used for standard spectrophotometric or polarimetric analysis, applicant's invention relies on the heretofore unrecognized principle that each element or compound has a recognizable and unique time variable pattern determined by the intensity of light that it transmits or reflects at various angles of polarization and at various wavelengths. Thus, the identity and concentration of a compound can be accurately determined by determining the intensity of light passing through or reflected by the compound per degree (or smaller unit) of polarization per wavelength per time dependency. Applicant's invention permits the practitioner to more accurately determine the constituent compounds of a specimen than is possible using conventional spectrophotometric analysis or by irradiating the specimen with monochromatic polarized light.

DETAILED DESCRIPTION OF THE PREFERRED EMBODIMENT

Figure 1:
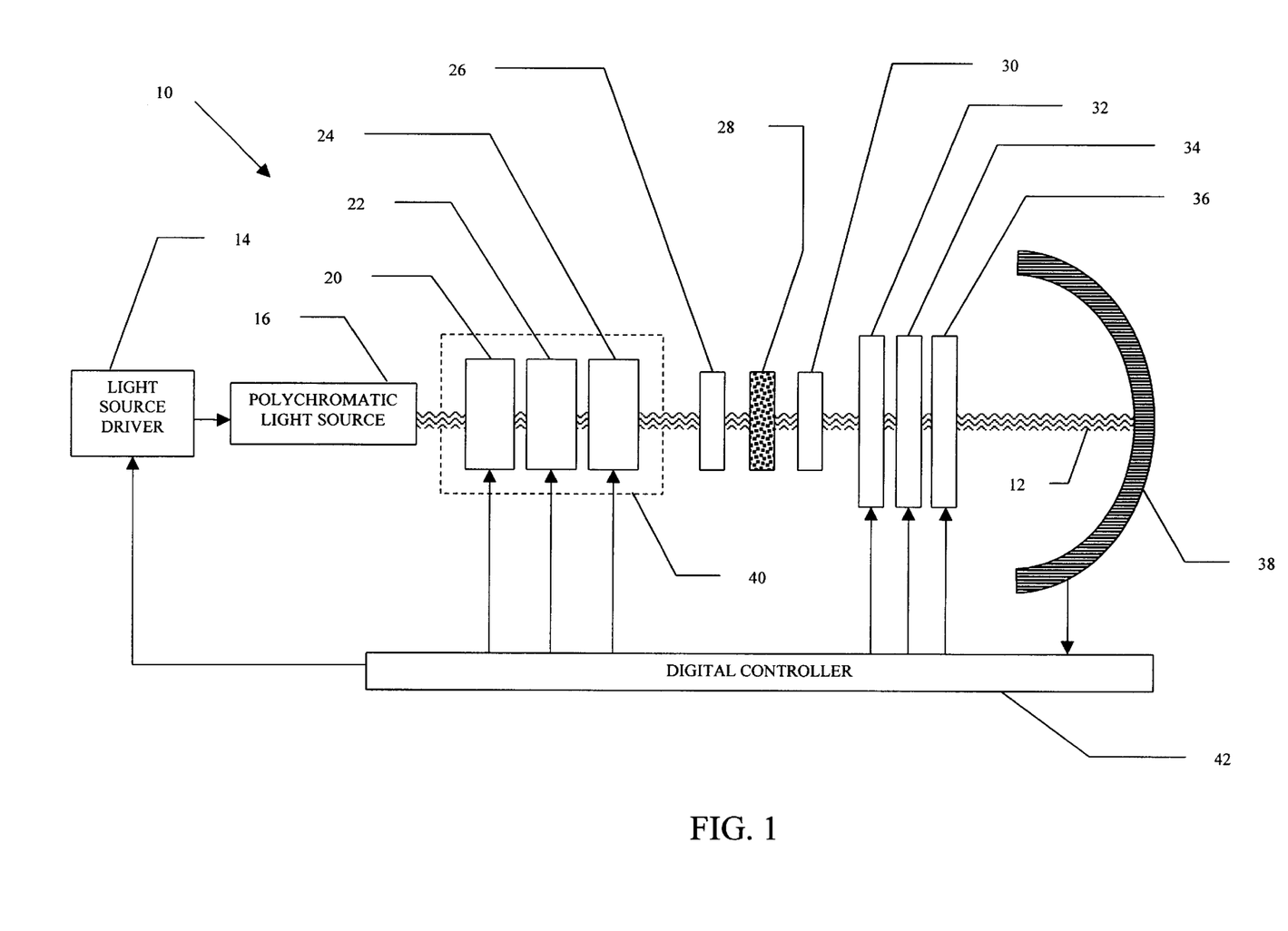
FIG. 1 is a schematic diagram representing the fundamental components of the system of the present invention incorporating a single light source.

Referring to FIG. 1, utilization of Applicant's invention involves configuring an array of optical instrumentation defining an optical path (10). The preferred embodiment of Applicant's invention will involve the components of optical path (10) being incorporated into a small, hand-held unit (not shown in the drawings). Optical path (10) includes polychromatic light source (16). Light source (16) in the preferred embodiment of Applicant's invention is a tungsten halogen lamp, but may be any suitably energized radiation source that creates appropriate partially polarized polychromatic radiation. The peak radiance of the light source in the preferred embodiment, when directed towards the detection of glucose occurs at a value of approximately 650 nm. The spectral range of primary relevance for the glucose measurements is 500 nm–1000 nm, thus making this an ideal source. The emitted light of this source is partially polarized, but with a dominant elliptical character due to its internal elliptically contoured reflecting mirror. In addition, randomly or partially polarized radiation, limited to specific range(s) of wavelengths, can be utilized through use of a light source, such as a laser source, or by the use of a monochrometer. Such a modification would be advantageous in particular applications, when a narrow frequency band of light is desired (most likely because of the particular light transmission properties of the analyzed specimens).

Polychromatic light source (16) is controlled by light source driver (14) which in the preferred embodimant is a switchable AC power source matched to the voltage and impedance of the light source (16). Light source driver (14) is itself regulated by digital controller (42), which in the preferred embodiment is a microprocessor based controller capable of retrieving a set of data and controlling the operation of both the incident light optical instruments and the reflected/transmitted light optical instruments, as described in more detail below.

Immediately adjacent to light source (16) is incident light pattern generator (40). In the preferred embodiment, pattern generator (40) is comprised of wavelength filter (20), polarizer (22) and LCD chopper (24). Together these optical devices provide the necessary incident light pattern appropriate for optimal interaction with the constituent compound of interest. Optimal in this case is defined as that pattern of incident light characteristics previously shown to interact with a specific constituent compound in a manner that provides a reflected/transmitted light pattern with easily identifiable benchmarks for establishing both the presence of the compound and its concentration.

Wavelength filter (20) may be any of a number of devices on the market that are capable of selectively passing light at specific wavelengths and with specific bandwidths. Controlled by digital controller (42), wavelength filter (20) operates to impart a modulated (or static if desired) pattern of wavelengths to the incident light beam.

Polarizer (22) may be any of a number of commercially available polarizers or may be a combination of specialized polarizing devices. As the present invention anticipates the modulation of both planar and circular polarization, polarizer (22) incorporates either optical devices capable of imparting such polarizations to a beam of light, or electromagnetic based polarizers capable of similarly effecting a modulated polarization in both the planar and circular modes.

LCD chopper (24) is the optical component designed to impart an amplitude modulation to the incident light beam. LCD choppers are solid state devices capable of establishing either aperature configurations or density filters that partially obstruct the incident beam of light. LCD chopper (24) and polarizer (22) are each controlled by digital controller (42) according to the pattern of incident light to be established for a particular constituent compound.

Finally, in the incident light section of optical path (10), wave guide (26) directs the incident light beam onto the specimen under investigation. In its simplest form, wave guide (26) may be a high quality lens that gathers and focuses the incident light beam onto the test specimen. More complicated structures could include fiber optics in order to provide a means whereby the optical path shown in FIG. 1 might be established with the need for a physically linear array of instrumentation. In fact, in one likely application of the system of the present invention, the test specimen (a human finger for example) is anticipated to be remote from the balance of the optical instuments associated with the optical path. In any event, test specimen (28) receives the incident light beam pattern established by the array of optical conditioners described above for a period of time defined by the optimal pattern for the compound under investigation.

The reflected/transmitted light section of optical path (10) is to a large degree configured as a mirror image of the incident light section. Wave guide (30) is positioned immediately adjacent to test specimen (28) and will typically be a device similar in structure and function to wave guide (26). Aperature (32) may be a device similar in structure and function to LCD chopper (24), although in the preferred embodiment, the requirements for amplitude modulation in the reflected/transmitted light are reduced and the need for selecting a specific spatial portion of the reflected/transmitted light beam is increased. Thus aperature (32) may be a mechanical aperature rather that the LCD aperature used in the incident light beam path. Wave length filter (34) may be the analog of wave length filter (20) in the incident light beam path.

Finally, polarizer (36) provides the necessary modulation of the polarization of the reflected/transmitted light beam necessary for analyzing the polarizing characteristics of the constituent compounds. Aperature (32), wave length filter (34), and polarizer (36) are each controlled by digital controller (42) in the manner described in more detail below, in order to effect an "analysis pattern" on the reflected/transmitted light beam that establishes readily identifiable "benchmarks" for the discrimination of a particular constituent compound and its concentration.

The result of the optical conditioning described above is a light beam pattern (12) that contains sufficient information in its characteristics to distinguish it from a large number of other patterns and make it unique to both the compound under study and the concentration of that compund within the test specimen. This light beam pattern (12) impinges upon and is "read" by sensor array (38) at the terminus of optical path (10). In the preferred embodiment, sensor array (38) is a plurality of light sensors mounted to a substrate in such a manner as to effectively capture relevant angles within the reflected/transmitted light beam. The specific function and structure of the array is described in more detail below in conjunction with a discussion of FIG. 3.

Figure 2:
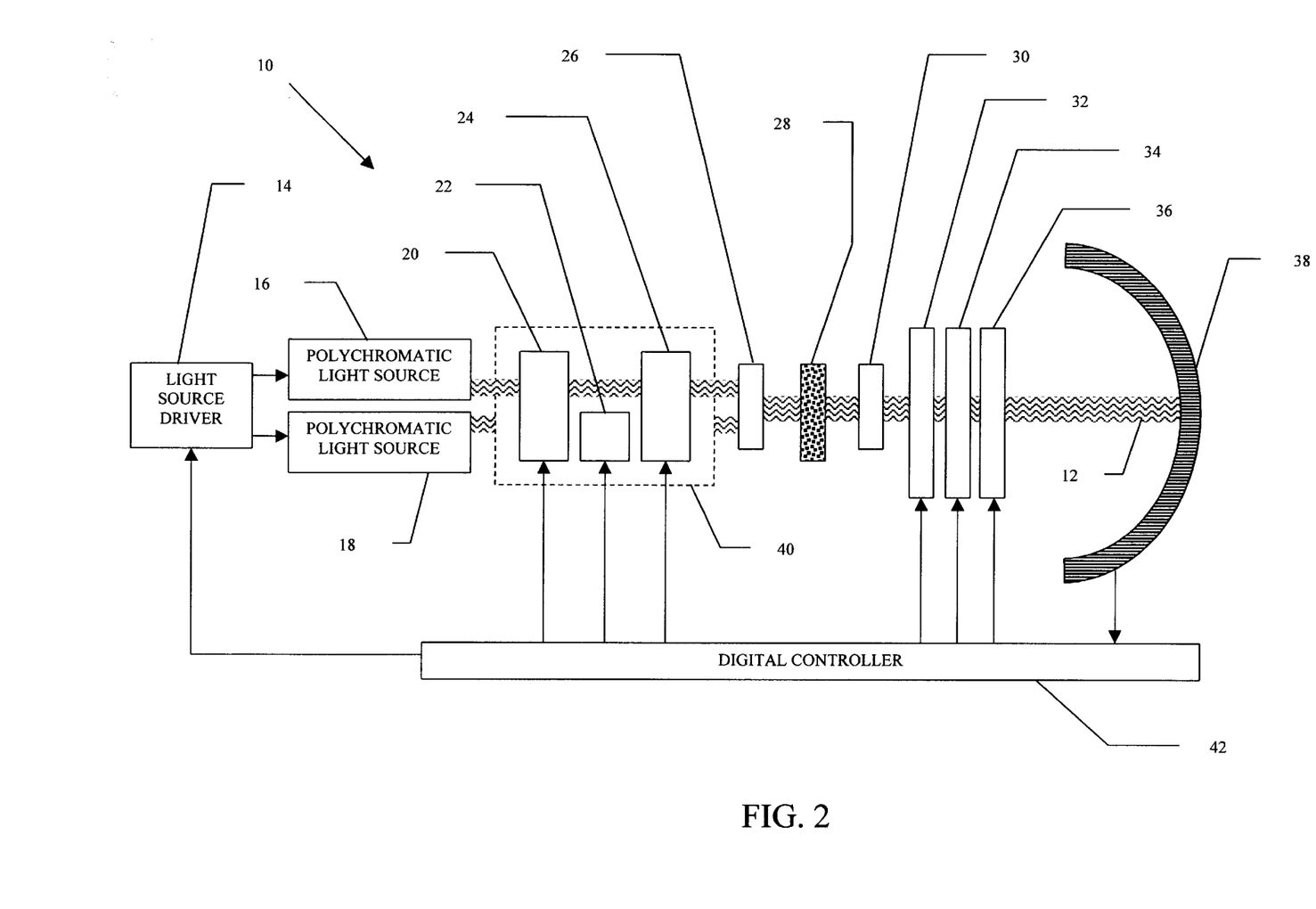
FIG. 2 is a schematic diagram representing the fundamental components of the system of the present invention incorporating two light sources.

Reference is now made briefly to FIG. 2 for a description of a modification of the optical path disclosed in FIG. 1 that may, in certain circumstances and with certain compounds of interest, provide a more effective mechanism for establishing an optimal interrogating light beam pattern. FIG. 2 is identical to FIG. 1 with the exception of the additional polychromatic light source (18) and the use of polarizer (22) with only one of the two resultant light beams. In this configuration, the methods of the present invention are better able to take advantage of characteristic patterns of incident light that use only partially polarized sources. It has been determined that the combination of polarized light (modulated) with unpolarized light to create an incident light beam that is partially polarized, provides the optimal pattern in many cases. The system structure disclosed in FIG. 2 provides this combination.

Figure 3:
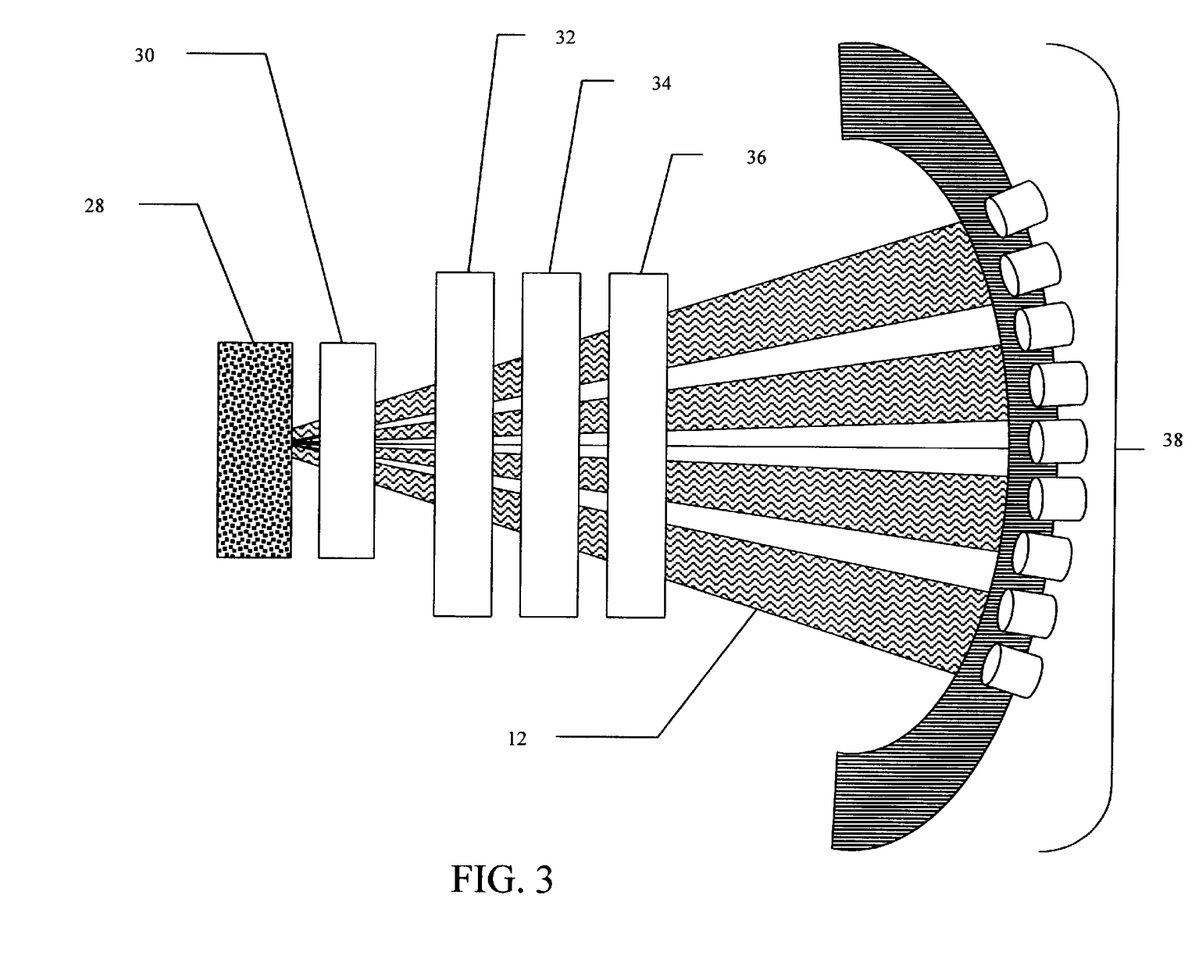
FIG. 3 is a detailed schematic diagram showing the analytical components of the system of the present invention and the pattern of light transmitted or reflected from the test specimen.

In FIG. 3 the divergant nature of the reflected/transmitted light beam can be seen. This divergent character is beneficial to the analysis of the pattern present in that it spreads the light beam out and "amplifies" the refractory properties of the molecules in the test specimen. Since it is a prior knowledge of the reflected/transmitted light pattern for a given compound in a given concentration that permits the re-identification of that same compound/concentration the only requirement for the method of spatially establishing the pattern and analyzing it is that it be repeatable. Thus for a given set of optical path instruments a specific compound/concentration with provide similar patterns capable of repeated detection and analysis.

Table 1 below provides a summary of the factors relevant for establishing an optimal modulated light pattern for both the incident light illuminating the test specimen and the reflected/transmitted light pattern used for analyzing the modifications brought about by the constituent compound under investigation.

TABLE 1

SUMMARY OF LIGHT FACTORS

| INCIDENT LIGHT | | TRANSMITTED/REFLECTED LIGHT | |
|---|---|---|---|
| MODULATED FACTORS | SYSTEM COMPONENTS | PATTERN FEATURES | SYSTEM COMPONENTS |
| Amplitude (Time Variable) | LCD Chopper | Amplitude | Sensor Array |
| Wavelengths (Time Variable) | Spectral Filter | Wavelength | Spectral Filter |
| Polarization (Planar) | Polarizer | Polarization (Degree) | Polarizer |
| Polarization (Circular) | Polarizer | Polarization (Rotation) | Polarizer |
| | | Spatial Angle | Sensor Array |

An example of the selection of these various factors for the optimal identification of a specific compound is disclosed in Table 2 below. Table 2 provides pattern information for the optimal identification of the presence and concentrations of Glucose in the blood. Analysis of concentrations levels are thus directly related to the intensity of the detected light pattern at specific spatil locations on the sensor array.

TABLE 2

| | POLARIZATION | | | | | | CHARACTER |
|---|---|---|---|---|---|---|---|
| ANALYTE | RT CIR | LFC IR | VER | HOR | WAVE LENGTH | AMPLI | (What to look for) |
| GLUCOSE | 50% | 50% Modulated at 10 Hz–100 MHz | 0% | 0% | 650 nm +/− 10% | unmodulated | * phase shift * amplitude * right circular dichromism |

Figure 4:
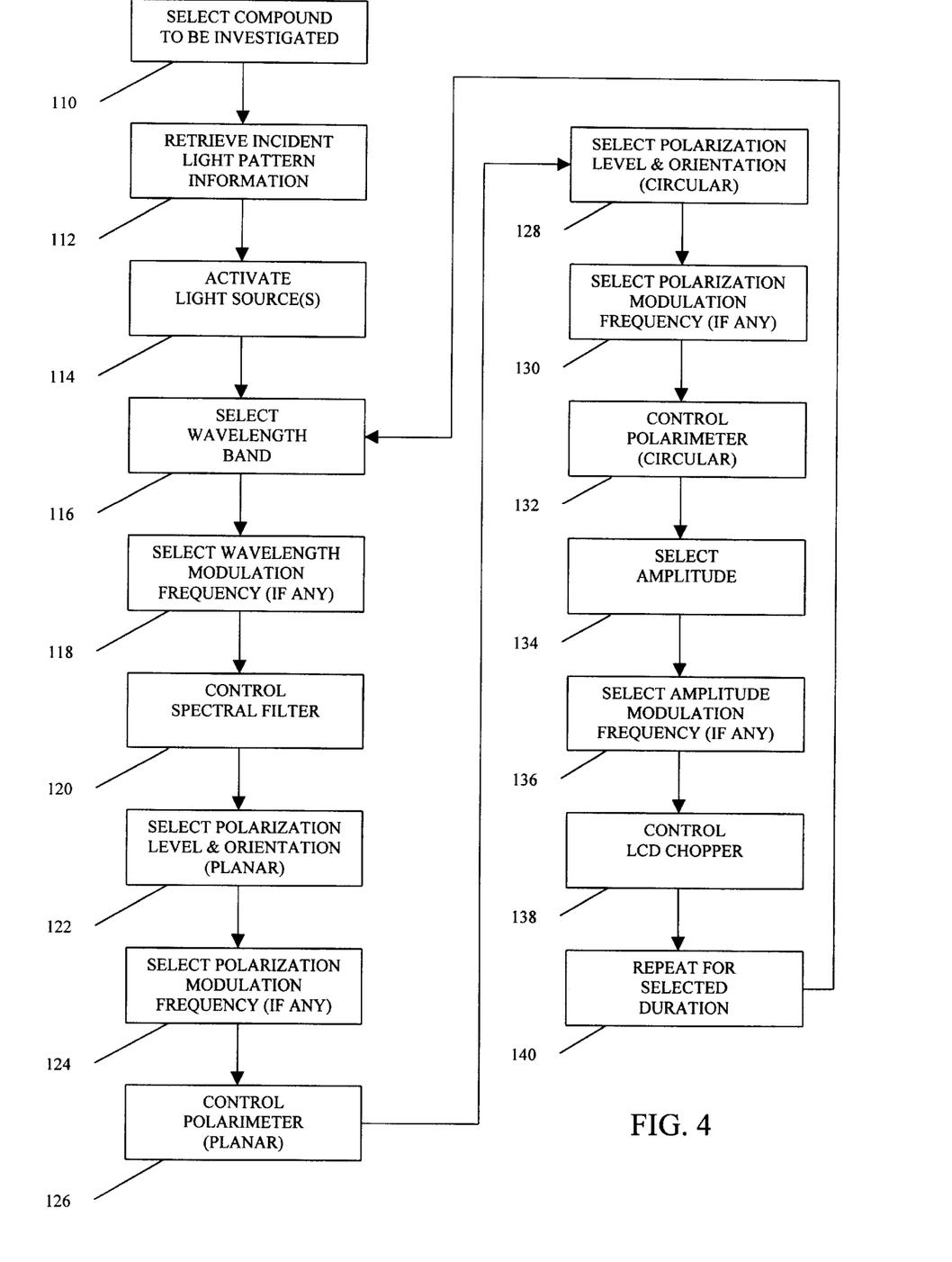
FIG. 4 is a flow chart showing the steps in the method of the present invention associated with generating an incident light pattern.

Reference is now made to FIG. 4 for a detailed description of the fundamental methodology of the present invention. Initially the method involves at step (110) the process of selecting the compound to be investigated. Under some circumstances the test operation associated with the method of the invention may have as its goal the quantification of a particular compound within a test specimen. The presence or quantities of other compounds in the test specimen may be irrelevant at the time. An example of this might be the situation where the goal of the system is to quantify glucose levels in the blood. In this case the sole compound to be investigated would be glucose and operation of the test method would be carried out once for that particular compound.

In other circumstances where a plurality of compounds are of interest, the process of the present invention might be carried out a number of times on the same test specimen in order to both identify and quantify a variety of compounds suspected to be present in the test specimen. An example of this might be in a drug testing situation where any of a variety of known compounds are anticipated. In such a case the methods shown in FIG. 4 and FIG. 5 would be repeated for each of the distinct compounds to be investigated. It is understood, therefore, that the method steps described hereinbelow would be repeated any number of times necessary to either verify a particular constituent compound or to cover each of the plurality of compounds of concern.

Once the particular compound to be investigated in the process has been selected the system, at step (112), retrieves incident light pattern information for that compound. As indicated above, one element of the present invention is an a priori knowledge of the characteristic light pattern behavior associated with a number of different compounds of interest. This a priori knowledge includes both the manipulative characteristics that a compound has on light and an optimal arrangement of characteristics for incident light for the purpose of investigating the presence and quantity of that particular compound. Simply stated, the methods of the present invention include not only the recognition of certain patterns of light transmitted or reflected by a compound within a test specimen but takes the process one step further by irradiating the test specimen with a specific incident light pattern known to result in a reflected/transmitted light pattern that is easily discernible and readily identifiable with the compound and its concentration. Step (112) in the method therefore involves the digital controller of the present invention retrieving stored data relating to the manner in which the digital controller will manipulate the incident light control devices in order to irradiate the test specimen with a particular incident light pattern. As described above, this incident light pattern involves modulated factors that include time variable amplitude, time variable wave length, planar polarization, and circular polarization. Various system components as described above accomplish the manipulation of the incident light in order to establish the above-described incident light pattern.

At step (114) the method proceeds to activate the light source or light sources, depending upon whether a single source or dual sources are required. In the preferred embodiment of the present invention it is anticipated that the light source itself will have a simple on/off configuration and that the time variable amplitude modulation factor will be controlled by an outside device such as an LCD chopper. For this reason, activation of the light source in step (114) by the digital controller simply initiates the optical path and does not itself contribute to establishing the incident light pattern characteristics beyond the characteristics already inherent in the polychromatic light source.

At step (116) the digital controller selects a wavelength band based upon the retrieved incident light pattern data. If, for example, the compound to be investigated is glucose, the wavelength band appropriate for the incident light pattern would be 650 nm plus or minus ten percent (10%) or approximately 585 nm to 715 nm. Again as indicated above, the selected wavelength band is a range of wavelengths previously identified as being particularly "active" in conjunction with molecules of the compounds under investigation. This activity may not be simply the transmission rate for those wavelengths and would more likely involve combinations of polarization effects, transmission, and differential absorption.

In any event, the particular wavelength band previously identified to provide an optimal incident light pattern is selected by the digital controller. Following from this at step (118), the digital controller identifies and selects any wavelength modulation frequency to be imparted to the selected wavelength band. Wavelength modulation involves either the process of scanning through the wavelength band selected or modifying the range of the band according to a known periodicity (frequency). Wavelength modulation may, for example, change the selected wavelength band from a very narrow range to a very broad band on a periodic basis. The digital controller of the present invention selects, based upon the optimum incident light pattern, a frequency at which this variation occurs. Such variations could also entail scanning across the wavelength band with a window range, again with a specific cycle frequency. It is additionally anticipated that the wavelength modulation function could involve a non-repetitive set of modulated cycles determined to be appropriate for optimal "scanning" of either a single compound or a plurality of compounds within the test specimen. In other words, it may be important to initially provide a wavelength modulation that scans the wavelength band width selected width, for example, a 50 nm window at a frequency of 20 cycles per second. This modulation could then be followed after a duration, by a modulated wavelength band width focusing on a central wavelength 650 nm, for example, with a 50 nm window (625 nm to 675 nm) and periodically varying the band width to a maximum plus or minus ten percent (10%) (585 nm to 715 nm).

The patterns possible for wavelength modulation are endless and are dictated by the characteristics of the compounds being investigated. Glucose for example requires little or no wavelength modulation in the manner described above, being optically active for a particular wavelength bandwidth sufficient to permit not only its identification but a determination of its concentration. Other, more complex optical compounds may require more complicated wavelength modulation characteristics in order to adequately identify the compounds through the selection of an incident light pattern.

The digital controller having retrieved the stored incident light pattern information selects and identifies the details of the wavelength modulation requirements. In step (120) digital controller operates to modify the characteristics of the spectral filter in the present invention in order to carry out the selected wavelength band from step (116) and the wavelength modulation frequency from step (118). In this manner the polychromatic light generated by the light source of the system provides a nearly endless variety of light patterns based upon the selection of a wavelength band and the modulation of that wavelength band selected.

Having accomplished one of the three primary modulated factors for the incident light (time variable wavelength modulation), the method of the present invention then proceeds to the step of modulating the polarization characteristics of the incident light. These steps involve modulating both planar polarization and circular polarization for the incident light. Initially at step (122) the digital controller selects the polarization level and orientation for planar polarization based upon the retrieved incident light pattern information. Here again the polarization modulation characteristics can be either complex or simple, depending upon the particular compound under investigation. Glucose, for example, requires no planar polarization within the incident light patterns since it responds best and is identified most easily through the use of circular polarization characteristics. For some compounds, however, planar polarization may provide the most efficient incident light pattern mechanism for identifying and quantifying the constituent concentration. Once a polarization level and orientation is selected at step (122), the system identifies and selects the modulation frequency, if any, for these polarization characteristics. As with the modulation of wavelength, the incident light pattern will include variable polarizations that in the preferred embodiment cycle through a selection known to be optimal for a particular compound. In the simplest situations, there may be no modulation or only a very gradual change in the polarization angle or degree of polarization for the incident light. As with the modulation of wavelength, there are nearly limitless possibilities with regard to the patterns for modulating planar polarization. The two basic features controlled by the polarizer include the above-mentioned polarization level and orientation. Modulation with respect to the polarizer orientation could comprise a scan through as much as 180° of orientation or could comprise a cycling through a specific range of directions. Modulation could also take the form of a simple switching back and forth between polarization orientations as between an orthogonal set of directions. For some compounds implementing polarization in orthogonal sets would have the effect of turning the light on and off for that compound without the actual diminution of the amplitude of the light.

In addition, the polarization level, i.e. the degree to which the light is polarized or unpolarized, may also be modulated with the polarizer of the system of the present invention. Thus, the modulation indicated in step (124) includes both the cycling of the level of polarization, if any, and the cycling of the angle of polarization. In both cases the digital controller of the system controls the polarimeter at step (126) with respect to planar polarization characteristics for the incident light.

The process then proceeds at step (128) to the control of circular polarization as has been determined critical for a number of compounds of interest. At step (128) the digital controller selects the polarization level and orientation for circular polarization based upon the retrieved incident light pattern information for the compound under investigation. At step (130) the circular polarization modulation frequency is selected, if any is to be applied. As with both the wavelength modulation and the planar polarization modulation, changes in the circular polarization characteristics of the incident light are entirely dependent upon the optimum patterns for a particular compound. Returning to the glucose example, optimum characteristics for the incident light include a fifty percent (50%) right circular polarization and a fifty percent (50%) left circular polarization modulated at a rate of 10 Hz to as much as 100 MHz. In any case the digital controller of the system directs the polarimeter at step (132) so as to control the circular polarization imparted to the incident light beam.

Finally, at step (134) the digital controller manipulates the amplitude of the light beam according to the requirements of the incident light pattern for the compound of interest. At step (136) the digital controller selects the amplitude modulation frequency, if any, and at step (138) controls the amplitude by effectively opening and closing a shutter provided by the LCD chopper of the present invention. The LCD chopper is a device suitable for manipulating the intensity of a light beam according to either fixed aperture configurations or partial obstruction filters. Once again, the modulation of the amplitude can be accomplished in any of a number of combinations associated with providing an aperture and/or providing an obstructing filter. It is known in the art that certain structures of apertures are capable of manipulating the spatial angle associated with an incident light beam. This feature in the present invention is beneficial for some compounds and detrimental to others. In general, it is preferable for the beam of light to be columnated up to the point at which it enters the test specimen and thereafter for the pattern of light to spread out for analysis. Certain apertures provided by the LCD chopper could inappropriately spread the beam prior to its illumination of the test specimen. In most situations, therefore, step (138) involving the control of the LCD chopper will comprise modulating the density of the LCD filter so as to obstruct more or less of the light beam directed through it.

After all the appropriate modulated features have been imparted to the light beam, the cycle of incident light pattern generation has begun. At step (140) the cycle is repeated for a selected duration, during which time the modulations of the wavelength, the planar polarization, the circular polarization, and the amplitude are carried out according to the pattern retrieved by the digital controller for the compound of interest. It can be seen from the above discussion regarding the modulation of the light pattern that extremely complex patterns could emerge for a particular compound of interest. Because of the number of variable factors associated with the incident light beam, there are literally an infinite number of patterns possible under the method of the present invention. Because the analysis of the reflected and transmitted light must be synchronized with the incident light pattern, it is clearly preferable for these patterns to be as simple as possible. In many instances, such as the example given for glucose, modulation for one or more of the incident light factors is eliminated or reduced to a very simple amplitude cycling. Glucose, for example, is detected by an optimal incident light pattern that includes modulated circular polarization but unmodulated wavelength and unmodulated amplitude.

Figure 5:
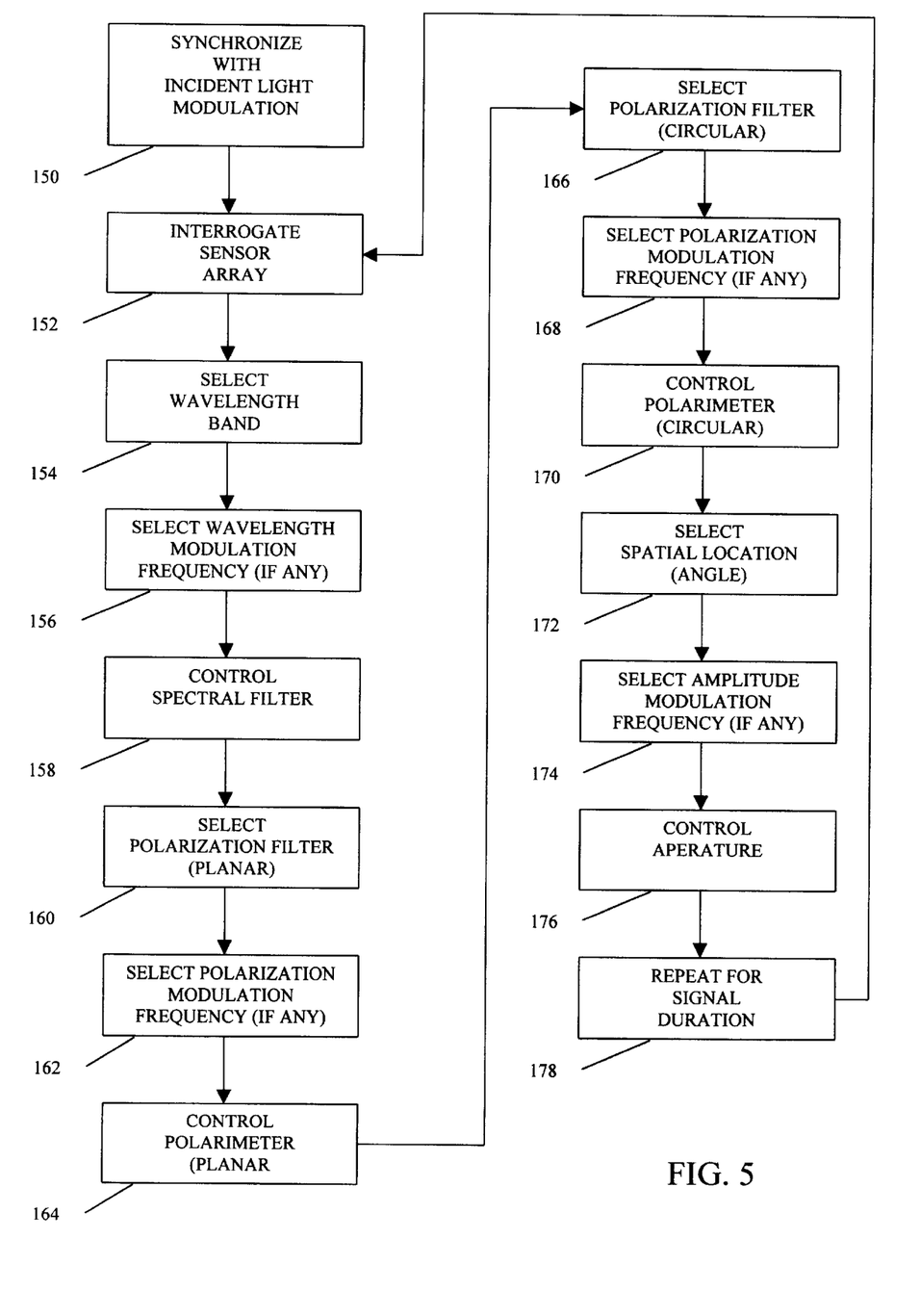
FIG. 5 is a flow chart showing the steps in the method of the present invention associated with analyzing the reflected or transmitted light patterns.

Reference is now made to FIG. 5 for a detailed description of the steps of the methods of the present invention associated with detecting and analyzing the reflected and transmitted light patterns after passage of the light beam through the test specimen. This process begins at step (150) by synchronization with the incident light modulation. As mentioned above, because there is a pattern to the incident light, it is essential that the detection and analysis process be synchronized with the incident light system in order to ensure that the modifications to the light beam caused by the test specimen are accurately detected and characterized. Since both the incident light beam and the light sensor array are controlled by the digital controller of the system of the present invention, this synchronization becomes inherent in the structure of the system. At step (152) the digital controller interrogates the sensor array and retrieves amplitude data from each of the sensors in this structural array.

To a great extent the process of controlling the light which strikes the sensor array is similar to the process of controlling the incident light illuminating the test specimen. Similar devices are operated by the digital controller so as to select and modulate the wavelengths of the light beam, its polarization both planar and circular, and its amplitude. It is recognized that perhaps the simplest form of the present invention allows the reflected/transmitted light from the test specimen to strike the sensor array unimpeded by the intervening control devices. Such as system would rely entirely upon the manipulation of the incident light beam to establish a pattern that could be recognized by the sensor array and retain enough detail as to not only distinguish the constituent compound but identify its concentration. Certain characteristics imparted to the reflected/transmitted light, however, are best detected when isolated from extraneous changes to the light beam brought about by other components to the test specimen. If, for example, a test specimen is illuminated with an incident light beam having wavelengths in a specific range, it is likely that the reflected/transmitted light beam will comprise components of light having wavelengths outside the incident range. Under some circumstances it might be desirable to select only a portion of the reflected/transmitted light wavelength spectrum for analysis and eliminate the remaining wavelengths from the sensor array. This is accomplished by selecting the wavelength band at step (154) shown in FIG. 5. The manner of this selection is essentially the same as the control of the spectral filter for incident light. As with the incident light beam, wavelength modulation may also be selected at step (156) in order to control and possibly synchronize the reflected/transmitted light with the incident light. All of this is accomplished at step (158) through the control of the spectral filter in the beam path subsequent to passage through the test specimen.

Again in a manner similar to the controller of the incident light beam, the planar polarization characteristics of the reflected/transmitted beam are also selected at step (160). The modulation of this planar polarization and the frequency of the modulation are selected at step (162). The polarization and its modulation are implemented through the control of the polarimeter at step (164). As indicated above, it is anticipated that a single polarimeter device is operative to modulate the planar polarization and the circular polarization for both the incident and the reflected/transmitted light beams.

At step (166) circular polarization characteristics are controlled for the reflected/transmitted light beam. Circular polarization filtering is selected and a modulation frequency, if any, is selected at step (168). Control of the polarimeter by the digital controller for the appropriate circular polarization is accomplished at step (170).

Finally, the spatial location of the light beam and the amplitude of the beam are selected at steps (172) and (174). Each of these steps involves the appropriate identification of pattern information for controlling the aperture positioned immediately before the sensor array in the system of the present invention. The aperture control is accomplished at step (176) and takes into account both the spatial location angle directed by the digital controller and the amplitude of the beam path in that direction. In this manner the amplitude of the beam path at a specific angle from the incident beam path can be controlled so as to provide a baseline for the sensor array to measure changes from the incident light pattern. The entire process of receiving the incident light wave according to the synchronized incident light pattern is repeated at step (178) for the duration specified in the test run. As described in conjunction with modulation of the incident light beam, the overall test operation could be a series of cycles through a pattern to find for a particular compound or a sequence of bench mark pattern manipulations known to optimally identify a particular compound. The various combinations of patterns and bench mark identification mechanisms are limitless.

It is anticipated that the actual identification of a compound and a quantification of the concentration of the compound would be accomplished by specifically looking at and quantifying bench mark sensor readouts at particular points in the cycling analysis of the reflected/transmitted beam. In this manner, a very complex incident light pattern can be analyzed subsequent to passing through the test specimen by interrogation of the sensor array at three or more very specific locations and points in time during the modulation cycle. The more discrete the incident light pattern is, the fewer individual interrogation of the sensor array might be required in order to accurately identify a constituent compound and its concentration. There is, therefore, a balance to be struck between the complexity of the incident light pattern and the number of interrogating sensor signals necessary to properly identify the compound. In the preferred embodiment of the present invention a moderately complex incident light pattern has been found to provide a sufficiently discrete and distinguishable reflected/transmitted light pattern that very few interrogating signals from the sensor array are required.

Although the invention has been described with reference to specific embodiments, this description is not meant to be construed in a limited sense. Various modifications of the disclosed embodiments, as well as alternative embodiments of the inventions, will become apparent to persons skilled in the art upon the reference to the description of the invention. It is, therefore, contemplated that the appended claims will cover such modifications that fall within the scope of the invention.

I claim:

1. A device for polychromatic polarimetric analysis of a test specimen, comprising:

means for irradiating a test specimen with partially polarized primary radiation beam;

means for modulating wavelength and bandwidth within said primary radiation beam;

means for modulating said partial polarization of said primary radiation beam;

means for modulating an amplitude of said primary radiation beam;

means for controlling said wavelength modulator, said polariztion modulator, and said amplitude modulator so as to impart a modulation pattern of light on said test specimen;

means for measuring an intensity of a secondary radiation beam reflected and transmitted by said test specimen as a result of being illuminated by said primary radiation beam, said measuring means operable at a plurality of spatial locations in the path of said secondary radiation beam; and means for identifying benchmark features in said measured secondary radiation beam, said benchmark features being light beam intensities at specific wavelengths in specific spatial locations at specific times relative to said modulated pattern of light imparted to said test specimen, said benchmark features being previously identified as indicative of specific constituent compounds in specific concentrations in said test specimen.

2. A method for performing a polychromatic polarimetric analysis of a test specimen, comprising the steps of:

irradiating a test specimen with a partially polarized primary radiation beam;

modulating the wavelength and bandwidth within said primary radiation beam;

modulating said partial polarization of said primary radiation beam;

modulating an amplitude of said primary radiation beam;

controlling said wavelength modulator, said polariztion modulator, and said amplitude modulator so as to impart a modulation pattern of light on said test specimen;

measuring an intensity of a secondary radiation beam reflected and transmitted by said test specimen as a result of being illuminated by said primary radiation beam, said measuring carried out at a plurality of spatial locations in the path of said secondary radiation beam; and identifying benchmark features in said measured secondary radiation beam, said benchmark features being light beam intensities at specific wavelengths in specific spatial locations at specific times relative to said modulated pattern of light imparted to said test specimen, said benchmark features being previously identified as indicative of specific constituent compounds in specific concentrations in said test specimen.

* * * * *